United States Patent [19]
St. Louis

[11] Patent Number: 5,649,727
[45] Date of Patent: Jul. 22, 1997

[54] CONTACT LENS HANDLING DEVICE

[76] Inventor: Jacques R. St. Louis, 2675 Liliane, Rockland, Ontario, Canada, K4K 1M3

[21] Appl. No.: 643,490

[22] Filed: May 6, 1996

[51] Int. Cl.⁶ .................................................. A61F 9/00
[52] U.S. Cl. ................................... 294/1.2; 294/64.1
[58] Field of Search ............................ 294/1.2, 64.1, 294/25; 271/90; 206/5.1

[56] References Cited

U.S. PATENT DOCUMENTS

| | | | |
|---|---|---|---|
| 2,850,279 | 9/1958 | Stoothoff et al. | 294/64.1 |
| 3,132,887 | 5/1964 | Martinez | 294/1.2 |
| 3,139,298 | 6/1964 | Grabiel | 294/1.2 |
| 3,154,306 | 10/1964 | Elliot et al. | 294/64.1 |
| 3,240,525 | 3/1966 | Wood | 294/64.1 |
| 3,424,486 | 1/1969 | Corley | 294/1.2 |
| 3,879,076 | 4/1975 | Barnett | 294/1.2 |
| 3,922,025 | 11/1975 | Updegraff | 294/1.2 |
| 4,026,591 | 5/1977 | Cleaveland | 294/1.2 |
| 4,079,976 | 3/1978 | Rainin et al. | 294/1.2 |
| 4,097,081 | 6/1978 | England | 294/1.2 |
| 4,126,345 | 11/1978 | List | 294/1.2 |
| 4,512,602 | 4/1985 | England | 294/1.2 |
| 5,192,070 | 3/1993 | Nagai et al. | 271/90 |
| 5,348,358 | 9/1994 | Selick | 294/1.2 |
| 5,456,508 | 10/1995 | Kozar | 294/1.2 |

FOREIGN PATENT DOCUMENTS

| | | | |
|---|---|---|---|
| 81/01239 | 5/1981 | WIPO | 294/1.2 |

*Primary Examiner*—Dean Kramer
*Attorney, Agent, or Firm*—R. J. Austin

[57] ABSTRACT

A suction cup for a contact lens holding device in which an inner curved surface of the cup has an outer continuous wall and a projection arrangement between the continuous and a centrally located aperture provided for air suction purposes. The projection arrangement is disposed to allow for air to be withdrawn through the aperture while providing a support for a lens as suction is applied. This cup, particularly for use with soft lenses, holds the lenses in position under suction without tending to draw the lenses at their centres into the aperture which would destroy suction. The projection arrangement may be a single wall. e.g. a spiral or a plurality of projections arranged in a particular manner for supporting the lens. The invention also includes a contact lens holding device having such a suction cup and a mouthpiece is preferably provided for the user to apply suction by insertion into his mouth.

11 Claims, 5 Drawing Sheets

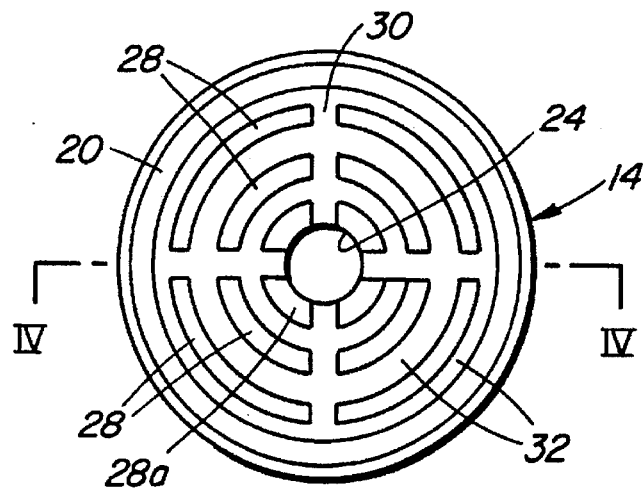
FIG. 3
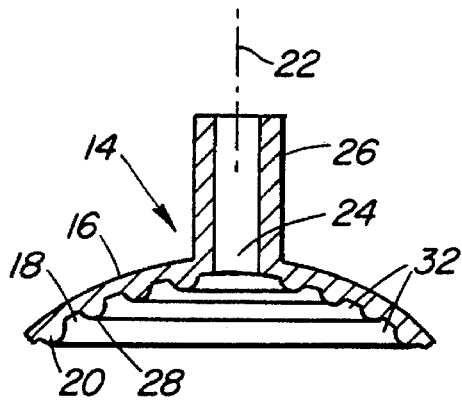
FIG. 4
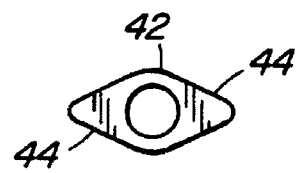
FIG. 5
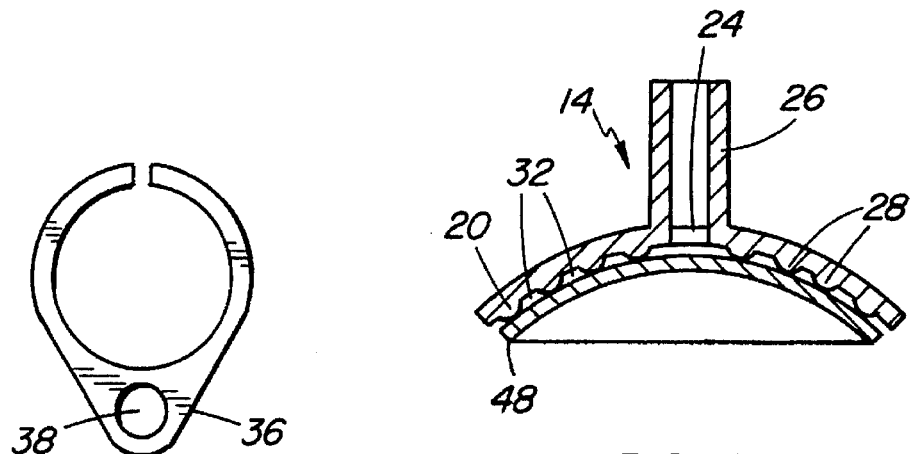
FIG. 6
FIG. 7

CONTACT LENS HANDLING DEVICE

This invention relates to contact lens handling devices.

Conventional contact lens handling devices for use in insertion and removal of contact lenses from in front of eyes include a type in which a suction cup is applied to a lens and vacuum is then created at a surface of the cup to hold the lens in the cup. With the cup mounted upon a handle structure, the lens is believed to be manageable for location in position in front of the eye and for its subsequent removal from the eye. One problem which attends use of known devices is that while such a device operates, in the main, successfully for so called "hard" contact lenses, its design and use is completely unsuitable for so called "soft" lenses. In this specification, "hard" lenses are recognized as lenses having a somewhat rigid characteristic whereas "soft" lenses which are becoming more acceptable, are lenses which are more flexible and are easier and more comfortable to use than "hard" lenses.

As persons skilled in the art are aware, hard contact lenses were the first to be commercially available and further commercial development produced "soft" lenses which are now increasing progressively in percentage of total sales of contact lenses in addition to the fact that the total sales of lenses are also increasing. However, while "soft" lenses are replacing "hard" lenses in use, there is a lack in the provision of suitable contact lens handling devices to enable users to insert and remove "soft" lenses. The conventional devices have suction cups with concave suction surfaces and a central opening to the surface from which air is withdrawn to create the necessary suction to hold the lens to the cup. Such conventional devices are show, for instance, in prior U.S. Pat. Nos. 3,424,486, 4,026,591, 4,097,081, 4,512,602, 5,348,358 and 5,456,508. This type of design is suitable for "hard" lenses which have their convex surfaces drawn on to the suction cup surfaces and held there when suction is provided. A slight resilient movement either by a "hard" lens or by a suction cup is sufficient to mate the opposing surfaces of the lens and the cup and to hold the lens in position. However, when such a suction cup is applied to a "soft" lens and suction is applied, the part of the lens centred over the central opening is drawn slightly into the opening as the flexibility of the soft lens allows for this. This action is accompanied by a flexing of the outer regions of the lens inwards and away from the surface of the suction cup. This inward flexing either has the effect of destroying the suction or it holds the lens in its deformed flexed state which renders it impossible or extremely difficult to fit the lens on to the eye. Also, it complicates the lens removal process.

In addition, in operation of conventional lens handling devices, vacuum is applied to the suction cup surfaces by hand operated suction devices. This complicates the operation of these devices in that one hand is required to hold the device with the fingers of that hand controlling the vacuum operation while the same hand is required to dispose the suction cup accurately in position either to release a contact lens onto an eye or to apply the suction cup against the lens prior to its removal. All these simultaneous actions imposed upon the same hand lead to difficulty in control of conventional lens handling devices which makes the operation of lens removal and insertion extremely tedious and troublesome.

The present invention seeks to provide a suction cup and a contact lens handling device including such a suction cup which may be used successfully for insertion and removal of "soft" contact lenses.

Accordingly, the present invention provides a suction cup for a contact lens handling device, the suction cup comprising a concave suction surface having an aperture therethrough for connection to a vacuum source, a continuous wall extending from the concave surface, the wall surrounding and spaced from the aperture, and the wall being of a size such that a contact lens may overlap and contact the wall, and a projection arrangement extending from the concave surface in locations between the wall and the aperture, the height of the projection arrangement being consistent with that of the wall, to enable a convex surface of the contact lens to sealingly engage around the wall and on the application of suction through the aperture, to cause the convex surface of the lens to be drawn against and be supported by the projection arrangement while being spaced from the concave surface with suction applied within the confines of the wall.

Suction cups according to the invention may be used successfully with soft contact lenses for insertion or removal thereof from the front of a person's eye. For use with hard lenses, it is preferable that the suction cup has a slight degree of resilient flexibility thereby enabling it to conform by small resilient deformation to the shape of the hard lenses when suction is applied so that the projection arrangement engages and supports such hard lenses. With the use of suction cups according to the invention with soft lenses, immediately suction is applied after the continuous wall engages the convex surface of the lens, suction takes effect throughout the whole suction chamber within the wall and between the lens and the convex surface of the cup to operate against the whole of the lens surface and draw the lens onto the projections. The suction chamber is thus created partly by the lens and partly by the cup. The lens is thus acted upon by the suction effect substantially across the whole of its convex surface. There is thus no tendency for suction at the aperture to pull on one portion of the lens and deform the lens away from the cup. As may be seen therefore, the invention is completely suitable both for hard and soft lenses.

The projection arrangement preferably comprises a plurality of projections which are of any shape and in any suitable relative locations to provide the required function of the device of the invention when in use. Preferably, the projections are elongate and extend around the aperture with gaps between the projections to allow for evacuation of air from around the projections and within the space bounded by the continuous wall. Also it is preferable that these elongate projections are arcuate and lie upon arcs of circles centred upon or close to the axis of the aperture of the suction cup. Alternatively the projections may comprise or consist of discrete localized projections spaced around the suction cup. The projection arrangement may, however, comprise a single projection which extends around the aperture while moving towards it. Such a projection may, for instance, follow the path of a spiral with spaced convolutions.

The invention also comprises a contact lens holding device comprising a tube having one end for connection to a vacuum source, and a suction cup for sealing attachment to the other end of the tube, the suction cup comprising a concave surface having an aperture therethrough interconnected with the inside of the tube, a continuous wall extending from the concave surface, the wall surrounding and spaced from the aperture, and the wall being of such a size that a contact lens may overlap and contact the wall, and a projection arrangement extending from the concave surface in locations between the wall and the aperture, the height of the projection arrangement being consistent with that of the wall to enable a convex surface of the contact lens to sealingly engage around the wall and, upon the application of suction through the aperture, to cause the convex surface of the lens to be drawn against and supported by the projection arrangement while being spaced from the concave surface to create a vacuum reduced chamber within the confines of the wall.

Preferably the contact lens holding device according to the invention is provided with a finger holding means for location upon the tube in a position adjacent to the suction cup for holding the user's finger to control the position and orientation of the cup. Preferably the finger holding means should be disposed such that a user's finger is directed axially of the tube. With such an arrangement, the end of the user's finger held by the holding means may be used for moving away an eyelid to assist in insertion and removal of a contact lens.

The finger holding means may be any means which will provide the desired function. Preferably the means is in the form of a ring which may be a continuous or split ring for insertion of the person's finger into the ring. A split ring may of course be resiliently flexible to accommodate different sizes of finger. A ring having a means for adjusting its diameter is also a possibility.

In addition, in a particularly preferred arrangement, the holding device of the invention has a mouthpiece at the end of the tube remote from the suction cup, the mouthpiece for insertion into the user's mouth whereby the user may provide suction to the suction cup surface by sucking air from within the tube. This arrangement is particularly advantageous as it avoids the necessity of the hand holding the device from operating a suction apparatus for holding the lens on to the suction cup. In practice, therefore, the user may have more manual control over the device for insertion and removal of the suction cup from in front of the eye.

Embodiments of the invention will now be described, by way of example, with reference to the accompanying drawings, in which:

FIG. 3 is a view in the same direction as FIG. 2 but to an enlarged scale of a suction cup forming part of the device of the first embodiment;

FIG. 4 is a cross-sectional view through the suction cup taken along line IV—1V in FIG. 3;

FIG. 5 is an end view of the device of the first embodiment taken in the direction of arrow V in FIG. 1;

FIG. 6 is a view in the direction of arrow 11 in FIG. 1 of a finger holding means of the device of the embodiment;

FIG. 7 is a view similar to FIG. 4 showing the suction cup holding a contact lens;

Figure 1:
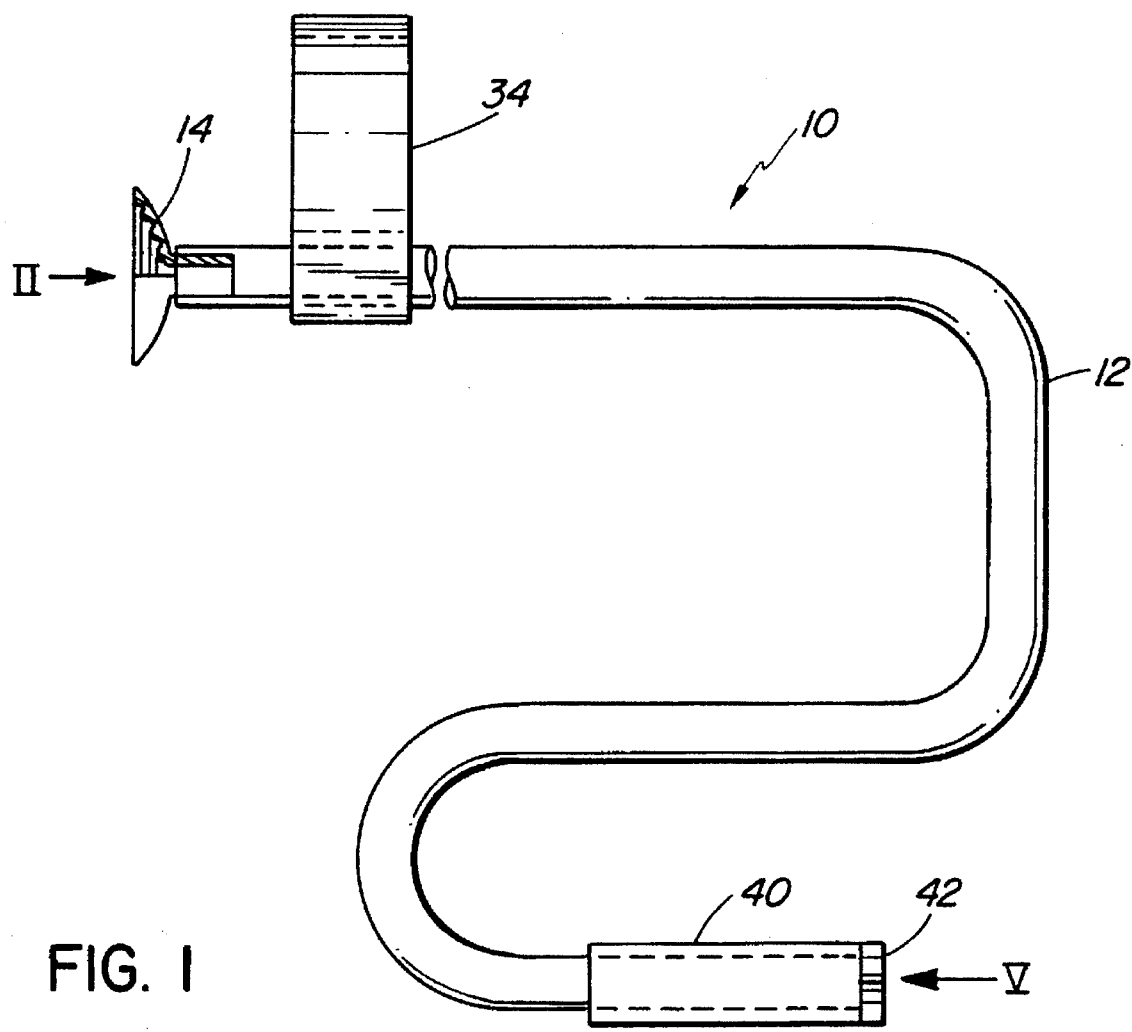
FIG. 1 is a side-elevational view of a contact lens holding device according to the embodiment.
Figure 2:
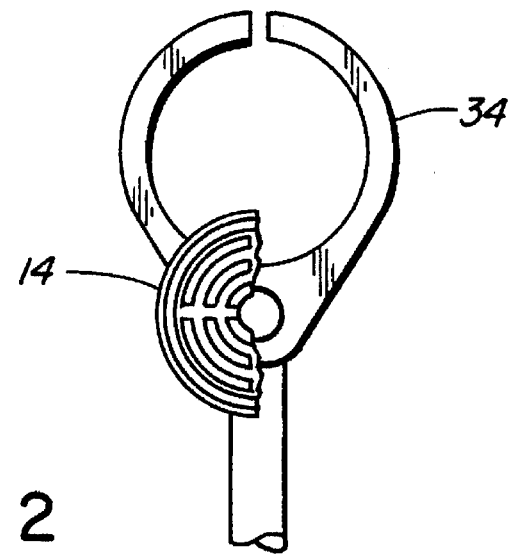
FIG. 2 is a view on the device in the direction of arrow 11 in FIG. 1.

In a first embodiment as shown in FIG. 1, a contact lens holding device 10 comprises a flexible rubber or plastic tube 12 of diameter suitable for comfortable insertion inside a user's mouth. At one end of the tube there is provided a suction cup 14. As shown by FIGS. 2, 3 and 4, the suction cup 14 has a part spherical body 16 having a concavely shaped inner surface 18 terminating at outer edges of the cup in a continuous circular wall 20 projecting inwardly of the surface 18. This wall 20 has a continuously smooth surface around its periphery and, in section as shown by FIG. 4, the surface of the wall 20 is convex and is formed upon the arc of a circle. The continuous wall 20 is centred upon an axis 22 which coincides with the axis of an aperture 24 extending outwardly from the convex side of the suction cup, the aperture 24 being continued as the bore within a tubular extension 26 also extending in the same direction.

Inwardly of the continuous wall 20 is provided a projection arrangement comprising a plurality of projections 28. Each of these projections in the embodiment is elongate as shown by FIG. 3 and follows the arc of a circle. The projections 28 are provided in three groups. The projections in each group have the same radius of curvature and lie upon the same pitch circle which is centred upon the axis 22, the groups decreasing in diameter inwardly of the continuous wall to terminate in an inner group 28a which lies close to the aperture 24. Each of the projections extends almost around 90 degrees of arc with the projections in each group being separated by a radially extending space 30, the spaces being aligned from group to group, and the groups of projections are separated by circular spaces 32 which are joined together by the spaces 30. All of the spaces extend inwardly to the concave surface 18 of the cup. The cup is secured tightly within the tube 12 by resilient reception of the tube around the tube extension 26 of the cup.

A finger holding means is provided by which the device is controlled in operation for insertion and removal of a contact lens in front of a person's eye. As shown by FIGS. 1, 2 and 6, the finger holding means comprises a resiliently flexible split ring 34 having at one side an enlargement 36 formed with a bore 38 which frictionally engages the tube 12 which is received therethrough. The ring 34 is axially directed in the same direction as the associated end of the tube 12.

At the other end of the tube 12 there is provided a mouthpiece for insertion in the user's mouth. This mouthpiece comprises a relatively short cylinder 40 which frictionally engages the outside of the tube 12 and at the end of the cylinder 40 remote from the tube 12 is disposed a mouthpiece end 42 which has two diametrically opposed flanges 44 extending radially outwards from the axis of the cylinder.

In use, the lens holding device of the first embodiment is held with a finger 46 of the user (FIG. 8) inserted through the ring 34 with the end of the finger directed towards the suction cup 14. With the mouthpiece end 42 held within the mouth, the suction cup is applied against the convex outer surface of a contact lens 48 (FIG. 7) and the user draws air inwardly to apply suction along the tube 12. This immediately creates suction between the lens and the suction cup and draws the lens on to the outer wall 20 and also on to the arcuate projections 28. Because of the smooth curved surface of the outer wall 20, the outer regions of the lens 48 become sealingly engaged against the wall and thereby a vacuum chamber is created between the cup and the convex surface of the lens. This, as shown by FIG. 7, ensures that the lens is drawn into supporting contact against each of the projections 28 while it is maintained in sealing engagement with the outer wall 20 and with the lens supported as a continuously smoothly curved dome. The suction to hold the lens in this position exists within all of the passages 32 and 30 of the suction cup surface. Although the lens may be a soft lens, there is no tendency for the lens to be drawn into the aperture 24 which would distort the shape of the lens and destroy any suction created thereby. This is because the suction is not only applied at the aperture 24 but has effect over the whole of the passages 30 and 32 so that the lens is drawn over the whole of its convex surface towards the suction cup and forms a sealed chamber for holding the lens effectively in position.

Figure 8:
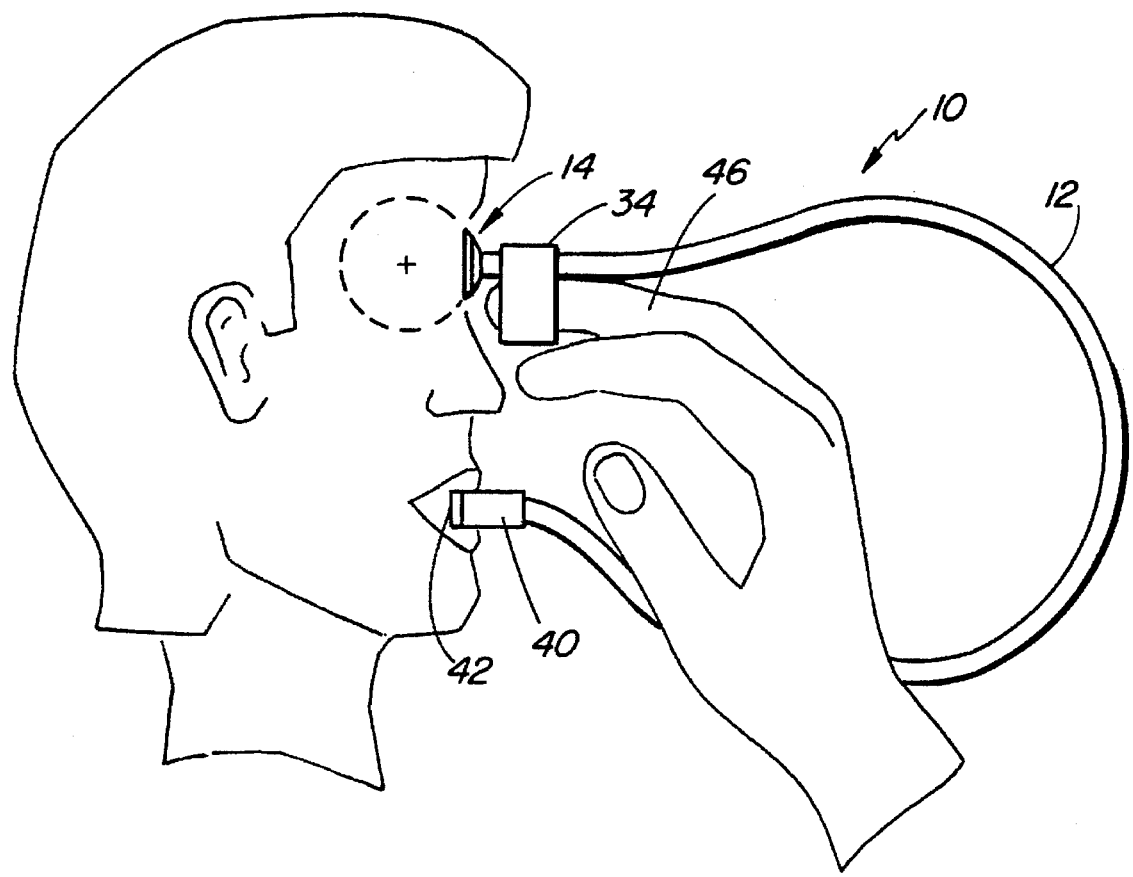
FIG. 8 is a side-elevational view with a person's head shown diagrammatically, illustrating the method of insertion and removal of a contact lens in front of the eye and using the device of the first embodiment.

While the user maintains the suction within the tube over a sufficiently short period, the lens is then applied to the surface of the eye, for instance as shown by FIG. 8. In this position, as may be seen, the finger 46 is directed towards the eye for benefit of position control and as will be noticed, this hand does not have to perform the dual function of lens insertion and control of a vacuum operating device. It follows therefore that the user needs only to control this hand for insertion of the lens and apart from movement of the hand to its correct location it may be retained in a substantially relaxed condition. The insertion of the lens may also be assisted by the use of the other hand (not shown) which may be necessary for the lifting of the eyelid from the user's eye for insertion of the lens. Once the lens is accurately inserted, the suction in the tube is relieved thereby enabling the cup to be removed from the lens.

Removal of the lens is performed in the reverse order from that discussed above in that the cup is applied to the lens in front of the eye, suction is applied by the user's mouth and the lens is then withdrawn upon the cup, the lens again providing with the cup a suction chamber as discussed above.

As may be seen from the above description the device of the embodiment is easy to use. No specific suction device is required as suction is applied by use of the user's mouth. This, of course, relieves the user's hand of any vacuum forming activity which simplifies the location of the lens within the eye. Furthermore, and of prime importance of course, is that a soft lens which is of extremely flexible nature may be held by vacuum upon the suction cup for its insertion and removal from in front of the eye. It is of paramount importance to realize that the distance between the projections is sufficiently close to prevent any flexing movement of the soft lens between the projections and which would destroy the sealing of the cup against the continuous wall 20.

Figure 9:
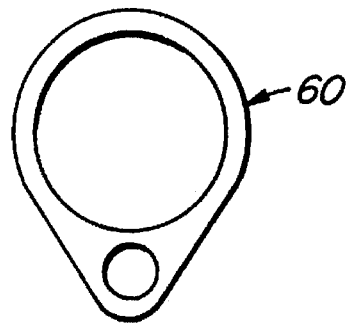
FIG. 9 is a view similar to FIG. 6 of a modification of the first embodiment.

The ring 34 in the embodiment need not be split. The ring could be a continuous ring as shown by ring 60 in FIG. 9 which may be resiliently flexible or of a rigid nature. However, when using the ring 60, it may be necessary to have a supply of rings of different diameter when sold in kit form particularly, so that any specific user of the device may have a choice of suitable ring for his own requirements.

Figure 10:
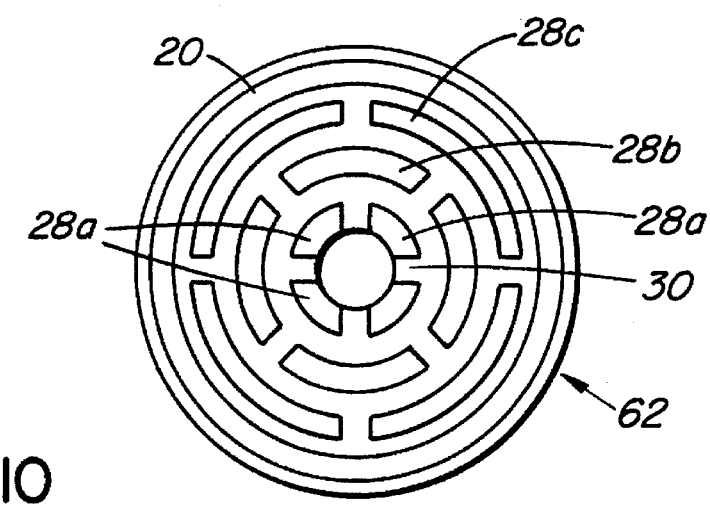
FIGS. 10 and 11 are views similar to FIG. 3 of suction cups used in contact lens holding devices according to second and third embodiments.

Also, the shape and position of the projections provided upon the suction cup need not necessarily be as described in the first embodiment. For instance, as shown in a second embodiment in FIG. 10 in which other parts of a contact lens holding device are as described in the first embodiment, a suction cup 62 is provided. This suction cup has a continuous wall 20 as described in the first embodiment and has a projection arrangement comprising projections 28 of the same size and shape as those discussed in the first embodiment. However, in the second embodiment of FIG. 10, as will be noticed, while these projections are provided in groups with the projections of each group on the same pitch circle diameter, the projections of the groups are not disposed in the same relationship as shown in the first embodiment. Thus, in the second embodiment, the gaps 30 between the centrally located group of projections 28b are not radially in alignment with the gaps of the other groups 28a and 28c. However vacuum may still be applied in that all of the gaps are connected by the spaces 32 so that complete evacuation of air may still take place from within the annular wall 20.

Figure 11:
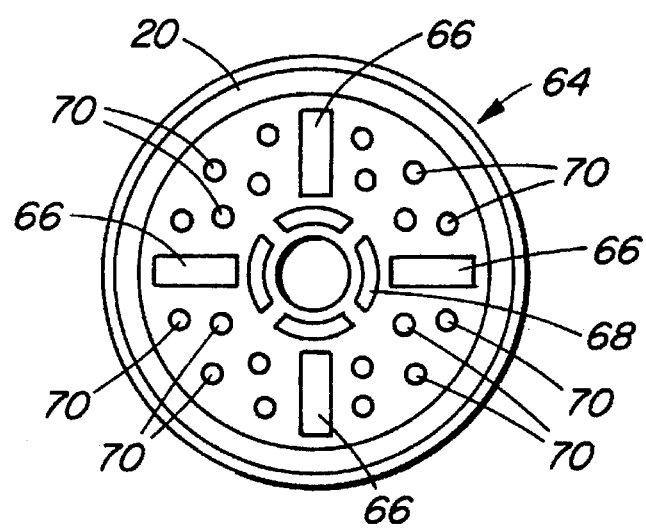

In a third embodiment as shown in FIG. 11 in which a contact lens holding device is otherwise similar to that described in the first embodiment, a suction cup 64 of the third embodiment while being provided with a continuous outer wall 20 as described in the first embodiment, has inner projections of completely different design. As shown in FIG. 11, the projections within the wall 20 comprise a plurality, namely four, radially extending projections 66 which are spaced at their outer ends from the wall 20 and at inner ends from arcuate walls 68 closely surrounding the aperture 24. The projections 66 are also spaced apart by discretely located projections 70. The elongate projections 66 thus diverge outwardly from the aperture 224 and between these projections 66 are provided more discreetly positioned projections 70. The projections 70 and the elongate projections 66 are again suitably located, of course, to ensure that a soft contact lens will not be drawn inwardly between the projections during the application of suction within the continuous wall 20 whereby continuous sealing contact of a lens against the continuous wall 20 is maintained pending the intended removal of suction from within the wall.

Figure 12:
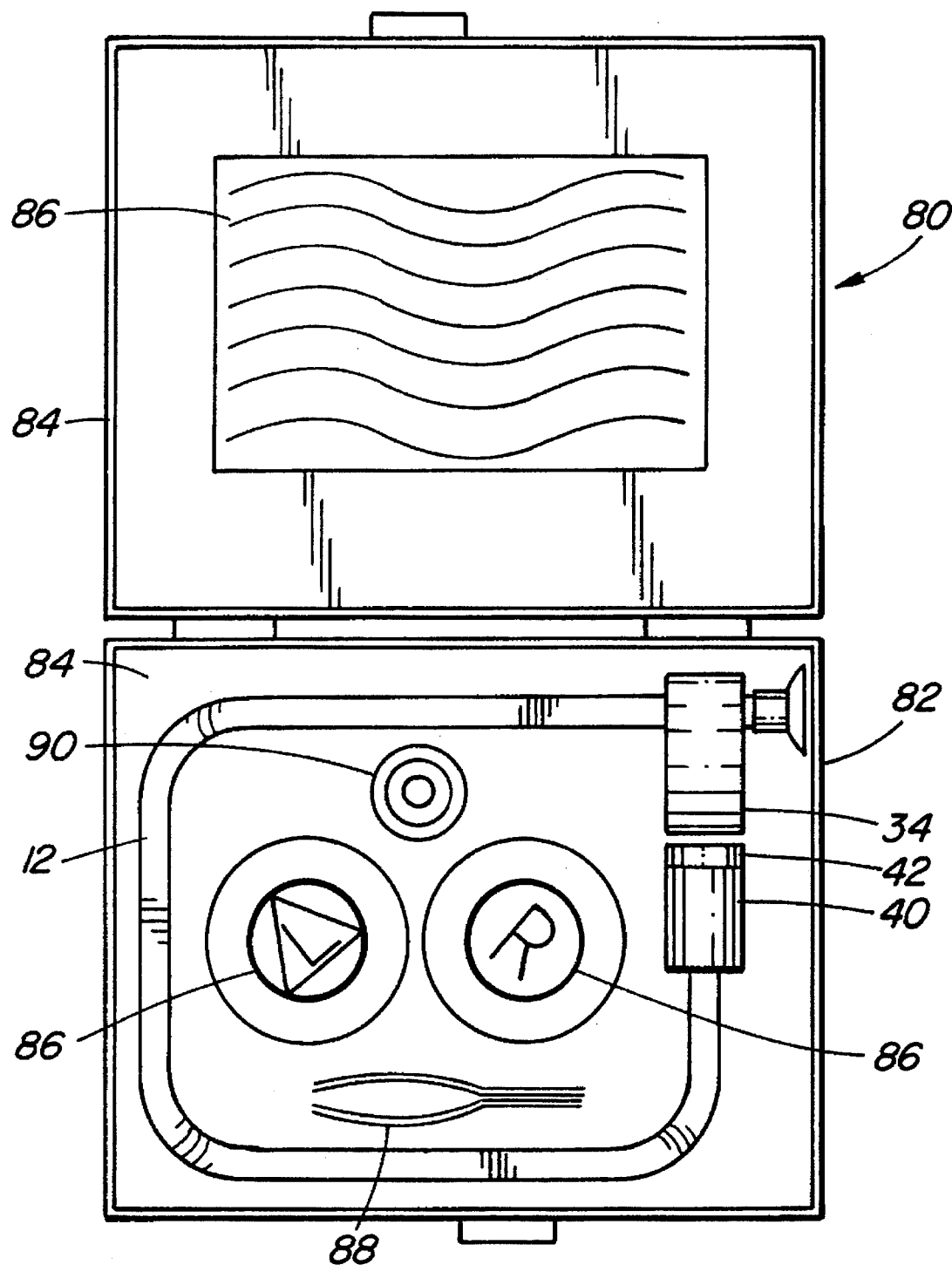
FIG. 12 is a plan view of an open container which may be used for storing devices according to the embodiments together with contact lenses.

Devices according to the invention and according to the embodiments described above may be conveniently carried in a storage container 80, for instance as shown in FIG. 12. The storage container 80 comprises a box 82 with a hinged lid 84, possibly provided with mirror 86. The box 82 has a molded bottom 84 in which depressions (not shown) are provided for holding the contact lens holding device (e.g. device 10 of the first embodiment) in position with the tube 12 extending around the box and having the mouth piece element 42 close to the ring 34. With this arrangement the tube 12 forms a boundary within which containers 86 may be located within suitable depressions, the containers provided one for each of the lenses. Also within the box is disposed a pair tweezers 88 and also, as a practical matter, the formation of the base of the box is provided with an upward domed area 90 of suitable size and shape for supporting a lens from within one of the boxes 86 preparatory to it being contacted by the suction cup 14 for removal from the dome and insertion in front of the appropriate eye of the user.

The embodiments of the invention in which an exclusive right or privilege is claimed are defined as follows:

1. A suction cup for a contact lens holding device, the cup having an aperture therethrough solely at a central region of the cup, the aperture extending to a generally inwardly curved surface having a continuous wall extending outwards from the curved surface, the continuous wall having a smooth surface for sealingly engaging a contact lens, the wall spaced around the aperture, and a projection arrangement also extending outwards from the inwardly curved surface in locations between the continuous wall and the aperture, the projection arrangement being located to enable air to be withdrawn through the aperture from the area bordered by the continuous wall, and the projection arrangement having a height consistent with that of the continuous wall and also having free outer edges which, at any diametrical cross-section of the cup, substantially coincide with a single arc which lies within the inwardly curved surface and which also coincides with a free outer edge of the continuous wall to enable a convex surface of the contact lens to be sealingly engaged by the wall with the contact lens supported as a continuously smoothly curved dome by the projection arrangement, whereby upon the application of suction through the aperture, suction chamber spaces are defined within the wall between the projection arrangement and defined partly by the lens.

2. A suction cup according to claim 1 wherein the projection arrangement comprises a plurality of projections which are elongate and extend around the aperture with gaps between the projections to allow for evacuation of air within the continuous wall.

3. A suction cup according to claim 2 wherein the elongate projections are provided in groups, the projections of each group extending around an arc of a circle and lying circumferentially in spaced positions upon a common pitch circle, with the projections of different groups lying on pitch circles one within another with the projections of the groups spaced apart from one another.

4. A suction cup according to claim 1 wherein the projection arrangement comprises a plurality of projections some at least of which are discretely located projections.

5. A contact lens holding device comprising a tube having one end for connection to a vacuum source, and a suction cup for sealing attachment to the other end of the tube, the suction cup having an aperture therethrough solely at a central region of the cup, the aperture extending to a generally inwardly curved surface having a continuous wall extending outwards from the curved surface, the continuous wall having a smooth surface for sealingly engaging a contact lens, the continuous wall spaced around the aperture, and a projection arrangement also extending outwards from the inwardly curved surface in locations between the continuous wall and the aperture, the projection arrangement enabling air to be withdrawn through the aperture from the area bordered by the continuous wall, and the projection arrangement having a height consistent with that of the continuous wall and also having free outer edges which, at any diametrical cross-section of the cup, substantially coincide with a single arc which lies within the inwardly curved surface and which also coincides with a free outer edge of the continuous wall whereby upon application of suction through the aperture, the contact lens will sealingly engage around the continuous wall and be supported upon the projection arrangement as a continuously smoothly curved dome while defining suction chamber spaces bordered by the continuous wall between the projection arrangement and defined partly by the lens.

6. A device according to claim 5 wherein the projection arrangement comprises a plurality of projections which are elongate and extend around the aperture with gaps between the projections to allow for the evacuation of air from within the continuous wall.

7. A device according to claim 6 wherein the elongate projections are provided in groups with the projections in each group lying on a common pitch circle with the pitch circles of different groups being of different diameter with the groups disposed radially one within another.

8. A device according to claim 5 provided with a finger holding means for location upon the tube adjacent to the suction cup for insertion of a user's finger to control the position and orientation of the cup.

9. A device according to claim 8 wherein the finger holding means is provided by a split ring which is resiliently flexible to accommodate and grip the finger of the user.

10. A device according to claim 8 wherein the finger holding means comprises a solid continuous ring.

11. A device according to claim 5 wherein the tube has a mouthpiece at the end remote from the suction cup, the mouthpiece provided for insertion into the mouth of the user to enable the user to draw air from within the cup and provide suction to hold the lens sealingly against the continuous wall.

* * * * *